United States Patent [19]

Webster et al.

[11] Patent Number: 4,542,751
[45] Date of Patent: Sep. 24, 1985

[54] SWEAT-COLLECTING DEVICE AND METHOD

[75] Inventors: Henry L. Webster; Wayne K. Barlow, both of Logan, Utah

[73] Assignee: Wescor, Inc., Logan, Utah

[21] Appl. No.: 459,838

[22] Filed: Jan. 21, 1983

Related U.S. Application Data

[63] Continuation-in-part of Ser. No. 358,012, Mar. 15, 1982, abandoned.

[51] Int. Cl.$^4$ ............................................. A61B 19/00
[52] U.S. Cl. ..................................... 128/760; 128/630; 604/75; 604/312
[58] Field of Search ............... 128/760, 767, 630, 632; 604/304, 308, 312, 315, 316, 327, 332, 338, 345, 346, 355, 356, 896, 897

[56] References Cited

U.S. PATENT DOCUMENTS

| | | | |
|---|---|---|---|
| 890,975 | 6/1908 | Gilbert | 604/75 |
| 2,652,827 | 9/1953 | Smith | 128/132 R |
| 3,635,213 | 1/1972 | Lahay | 128/632 |
| 3,862,627 | 1/1975 | Hans, Sr. | 128/643 |
| 3,900,018 | 8/1975 | Piunno | 128/1 R |
| 4,190,060 | 2/1980 | Greenleaf et al. | 604/312 X |
| 4,311,050 | 1/1982 | Bessman | 604/73 X |
| 4,393,873 | 7/1983 | Nawash et al. | 604/174 X |
| 4,398,543 | 8/1983 | Sandlin et al. | 128/760 |

OTHER PUBLICATIONS

Gibson, L. E., di Sant'Agnese, P. A. "Studies of Salt Excretion in Sweat", *J. of Pediatrics*, vol. 62, No. 6, (Jun. 1963), pp. 855-867.

*Primary Examiner*—Edward M. Coven
*Attorney, Agent, or Firm*—Mallinckrodt, Mallinckrodt, Russell & Osburn

[57] ABSTRACT

A sweat-collection device formed as a solid body having a shallowly concave, sweat-collecting surface at a face thereof defining a concavity with a rim lying wholly within a common plane for firm placement over an iontophoresis-stimulated area of a person's skin to collect sweat from the skin area and pass it through a bore at the center of the concavity. The concavity is so shallow that no dead space occurs between the collecting surface and the skin and flesh bulged into the concavity when the device is applied to a patient whose sweat is to be collected for testing. Optionally, the concavity may be modified without introducing dead space thereinto, to incorporate barrier means for preventing unusually soft skin and flesh of infants and some adults from bulging into and closing the bore. A length of flexible tubing is secured to the axial bore for receiving and storing the collected sweat, and a chamber may be provided in the body of the device opposite the sweat-collecting surface for receiving and holding the tubing in flat coiled condition. A strap is provided for securing the device to a patient whose sweat is to be tested. Provision is preferably made for retaining, in and for discharging from the tubing, sweat after it has been collected.

26 Claims, 12 Drawing Figures

SWEAT-COLLECTING DEVICE AND METHOD

RELATED APPLICATION

The present application is a continuation-in-part of copending application Ser. No. 358,012, filed Mar. 15, 1982, now abandoned.

BACKGROUND OF THE INVENTION

1. Field

The invention is concerned with the collection of human sweat for medical evaluation and is particularly directed to the providing of a new sweat collection device.

2. State of the Art

For many years it has been known that the concentrations of sodium and chloride are considerably above normal in the sweat of children suffering from cystic fibrosis of the pancreas.

In recent years, it has been common to induce sweating in a localized area of a person's body by an iontophoretic application of a drug such as pilocarpine nitrate. Under one sweat-collection method, the stimulated skin area is covered by a preweighed, salt-free, gauze pad which is held in place by a sheet of plastic sealed to the patient such that the sweat produced in the covered area is collected in the gauze pad. After approximately 45 minutes or longer the pad is quickly removed and re-weighed, after which the sweat is eluted into an aqueous solution for analysis, taking care not to allow evaporation of any of the sweat, since sweat evaporation results in artificially high concentrations of sodium and chloride.

More recently, it has been discovered that electrical conductivity and osmolality measurements of sweat are also useful for determining increased sodium and chloride concentrations. An advantage of these methods is that a much smaller volume of sweat can be used than is required by the gauze method, and it has been common practice to sealingly secure a small inverted cup over the pilocarpine-treated skin area for the collection of the secreted sweat. Sweat droplets form on the skin covered by the cup and are collected for analysis by tilting the cup and scraping the skin-contacting portions of the cup's rim across the skin to pool the droplets and force the pooled sweat into the cup. This method of collection has suffered, however, by reason of condensation on the interior of the cup, which introduces major error in the results of the analysis. Also, a large surface area of sweat is exposed when the cup is removed, thus making it necessary to work rapidly when collecting the sweat so that salt concentration will not be artificially high.

Use of a cup for sweat-collection also poses the problem of determining how much sweat will be collected, since some persons sweat much more than others. Thus, just prior to removing a cup, one is never sure whether or not a sufficient quantity of sweat has been collected.

A heated sweat cup as described in U.S. Pat. No. 4,266,556 has eliminated the serious problem of error caused by condensation. It provides an error-free sample of the patient's sweat. However, as with any cup device for collecting sweat and even though a practitioner can become very adept with practice, it is difficult to avoid loss of sweat during scraping, and error may arise from inclusion of sweat, concentrated by evaporation, that borders the area covered by the cup.

Although the heated cup must be recognized as a major advance in sweat collection devices, there has been one other negative factor connected with its use. It should be realied that the patients who are tested for cystic fibrosis are generally quite young. The iontophoresis step requires the patient to be "attached" to an electrical power source for several minutes. Use of a heated cup extends this time by some fifteen minutes more, a length of time which may seem interminable to a child.

A quite different sweat-collecting device was used early in the 1960's for experimental purposes in simultaneously measuring the rate of sweating and the salt concentration of the sweat. It is described and schematically illustrated in the June 1963 issue of "The Journal of Pediatrics", pages 855–867, in an article entitled "Studies of Salt Excretion in Sweat" by Lewis E. Gibson and Paul A. di Sant' Agnese. This device comprised a shaped, cylindrical block of transparent "Lucite" plastic, having a concave bottom surface bordered by an annular flat margin for direct application to the skin of a patient as a sweat collector. Sweat produced within the area covered by the concavity was forced into an elongate, transparent, measuring tube connected to an axial bore leading upwardly from the center of the concavity. Salt concentration of the sweat was determined by means of two electrodes extending into the axial bore in spaced relationship lengthwise of the bore to measure electrical conductivity of the sweat in the bore. Periodically, sweat was removed from the device by means of a syringe connected to a so-called "pull-off" tube that intersected the bore below the electrodes. The total sweat sample obtained by the syringe was subjected to electrical conductivity measurement to determine average conductivity and was analyzed photometrically for salt content.

This device had what the experimenters termed "dead space", which included space between the skin of the person being tested and the concave sweat-collecting surface of the device. Although this was recognized as a source of possible error in test results obtained by experimental use of the device and was taken into consideration in test calculations made, it represents a loss of sweat volume which could be serious in the routine medical laboratory use of a device of this kind.

Thus, sweat loss due to dead space ranged from 8.8 to 42.1 microliters and averaged 20.3 microliters. Since the average patient normally produces a total volume of only 50–60 microliters of sweat during an entire period of collection, losses of such magnitude cannot be regarded as insignificant. Moreover, the sweat collected under these circumstances is not representative, since the rate of sweat production decreases with time after pilocarpine stimulation, and salt concentration in the sweat depends upon the rate of sweat formation in the individual.

Although a device of this kind might seem to offer advantages over other sweat-collection devices, its limitations preclude practical application other than the experimental use described.

SUMMARY OF THE INVENTION

The device of the present invention has structural similarities to that of the experimental Gibson et al. sweat-collecting device. Thus, it comprises a sweat-collecting body having a concave undersurface which may or may not be bordered by a flat peripheral margin. Also, an axial bore is positioned at the center of the concavity to provide for removal of sweat collected within the concavity. However, we have found that the amount of dead space within the concavity is related to the overall height of the concavity and that, by significantly decreasing this height, the dead space can be effectively eliminated. In addition, we have found that the collected sweat can be conveniently stored and removed for analysis in a length of flexible tubing connected with the axial bore externally of the concavity and compactly held by the body of the device while awaiting use.

The flexible tubing as so connected is preferably coiled in flat spiral formation for compactness, and provision is advantageously made for retaining the coiled tubing in a receiving recess formed on the back of the sweat-collecting body. Additionally, provision is made for securely attaching the device to a patient, as by a size-adjustable strap to be fastened around a limb of the patient.

A modification of the device for use on infants and adults having unusually soft-skinned flesh resides in the provision, at the entrance of the bore leading from the concavity, of barrier means against skin and flesh intrusion into such entrance of the bore. The barrier means may take various forms, such as radial ribs protruding into the concavity and tapering outwardly a relatively short distance from the periphery of the bore, or corresponding recesses in the concave surface defining the concavity. Such means may even be a permeable paper disc covering the bore entrance, but this is not favored since it involves placement of a separate item during application of the device to a patient. We have not been able to detect any dead space within the concavity in the use of these modifications.

In use of the device, after a desired amount of sweat has been collected in the coiled tubing, such tubing is detached from the bore, either by pulling it free of the bore in those instances in which the end of the tubing is merely inserted into and frictionally held by the bore, or by severing it with a sharp knife at the bore, the latter entailing only a very small loss of sweat contained within the tubing over the length of the bore. Opposite ends of the tubing are closed, for example, by forming the tubing into a closed loop and attaching its opposite ends to the opposite ends of a relatively short length of rigid tubing, such as stainlss steel. In this way, the collected sweat is removed and held intact for carrying to the laboratory for determination of salt concentration at an appropriate time.

To transfer the collected sweat to a testing vessel, it is advantageous to attach an elastomeric bulb to one end of a second length of rigid tubing and to then attach the other end of the rigid tube to the free end of the sweat-collector tubing after it has been disconnected from the closed loop position. By carefully squeezing the elastomeric bulb, a required quantity of the collected sweat can be conveniently deposited into the testing vessel by way of the short rigid tube at the opposite end of such disconnected sweat-collector tubing.

A better way of accomplishing this, however, is to form an elastomeric bulb by attaching a short length of a relatively large diameter, flexible plastic tubing to the hubs of two blunt hypodermic needles, close the passage through one of the needles, and attach opposite ends of the sweat-filled collecter tubing to the respective needle shanks. For discharge of the sweat, the tubing end attached to the closed needle is detached and used as the discharge end.

THE DRAWINGS

In the accompanying drawings, which represent the best mode and variations thereof as presently contemplated for carrying out the invention:

FIG. 1 is a view in axial, vertical section showing one embodiment of the device on a considerably larger scale than actual size, the diameter of the sweat-collector tubing shown as attached to the sweat-collecting body and the extent of concavity of the concave sweat-collecting surface of the sweat-collecting body being exaggerated;

FIG. 2, a bottom plan view of the device of FIG. 1 drawn to a much smaller scale, but still larger than would normally be actual size;

FIG. 3, a view similar to that of FIG. 2, but in top plan;

FIG. 4, a fragmentary perspective view showing the device secured to the forearm of a patient;

FIG. 5, a fragmentary longitudinal section showing how the collector tubing is formed into a closed loop for storage;

FIG. 6, a similar view showing how sweat is transferred from the collector tubing to a testing vessel after disconnection of the closed loop;

FIG. 7, a view corresponding to that of FIG. 1 but illustrating a somewhat different embodiment of the device;

FIG. 8, a view corresponding to that of FIG. 2, but of the device of FIG. 7;

FIG. 9, a view corresponding to that of FIG. 3, but again of the device of FIG. 7;

FIG. 10, a fragmentary sectional view taken along the line 10—10 of FIG. 8, showing radial ribs protruding into the concavity from the concave surface as barriers to skin and flesh intrusion into the bore entrance;

FIG. 11, a similar view showing similarly formed recesses in the concave surface as barriers to skin and flesh intrusion into the bore entrance; and FIG. 12, a view corresponding to that of FIG. 5, but showing a preferred alternative arrangement.

DETAILED DESCRIPTION OF THE ILLUSTRATED EMBODIMENTS

Figure 1:
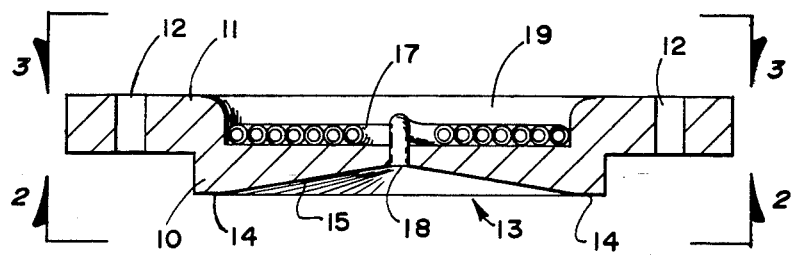
Figure 2:
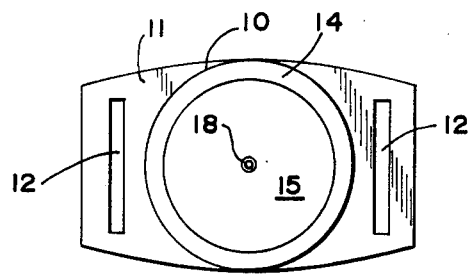
Figure 3:
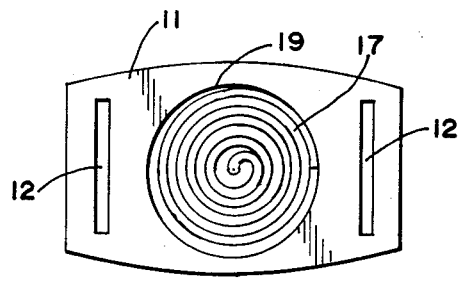

In the illustrated form shown in FIGS. 1-3, the device of the invention comprises a solid, sweat-collecting body advantageously molded to shape from a suitable plastic material, such as polyethylene or polystyrene, and including a portion 10 of disc formation projecting integrally from a back portion formed as a backing plate 11 provided with slot-like openings 12 at opposite ends thereof for the reception of straps constituting means for attaching the device to a person.

The face of sweat-collecting body portion 10 has a shallow concavity 13 whose rim 14 lies wholly in a common plane and which is defined by a broad, sweat-collecting, concave surface 15. Preferably, and as here illustrated, concavity 13 is of squat conical formation, having a broad base and very short altitude. Rim 14 is a flat annulus in this illustrated embodiment.

Such concave face of body portion 10 is adapted to be placed and held firmly against the surface of a patient's skin by a size-adjustable strap 16, whose ends are secured in slots 12. A coiled length of flexible, sweat-collector tubing 17 is shown as having one of its ends fitted into or otherwise connected to a bore 18, which extends axially through the body portion 10 and communicates with concavity 13 at the apex of concave, sweat-collecting surface 15.

Provision is preferably made for retention of sweat-collector tubing 17 in compactly coiled form at the back of the body by recessing backing plate portion 11 in the form of a circular chamber 19 overlying sweat-collecting surface 15. Tubing 17 is coiled in flat spiral formation and placed in the receiving chamber 19. This feature of the invention, it should be noted, may be advantageously utilized apart from other features explained herebelow.

Although rim 14 of concavity 13 is here shown as a flat annulus having substantial width between its inner and outer diameters, the width of the annulus can be reduced to an annular edge without affecting the efficacy of the invention.

Figure 4:
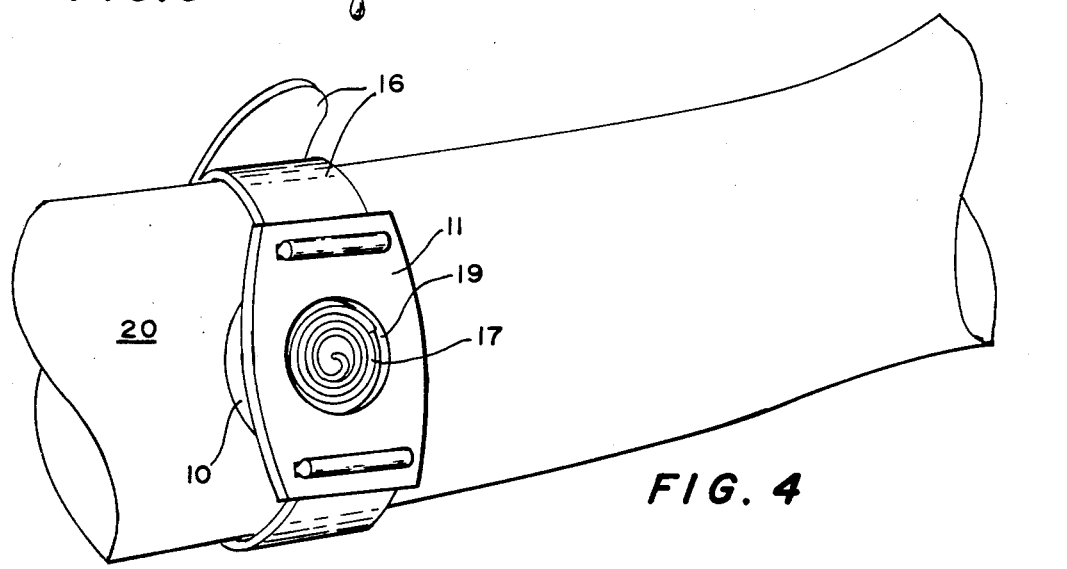
Figure 7:
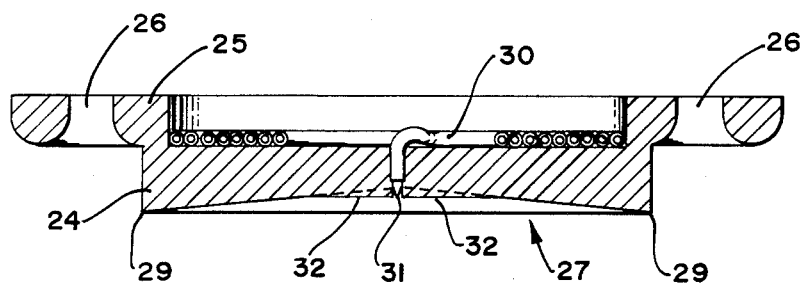
Figure 8:
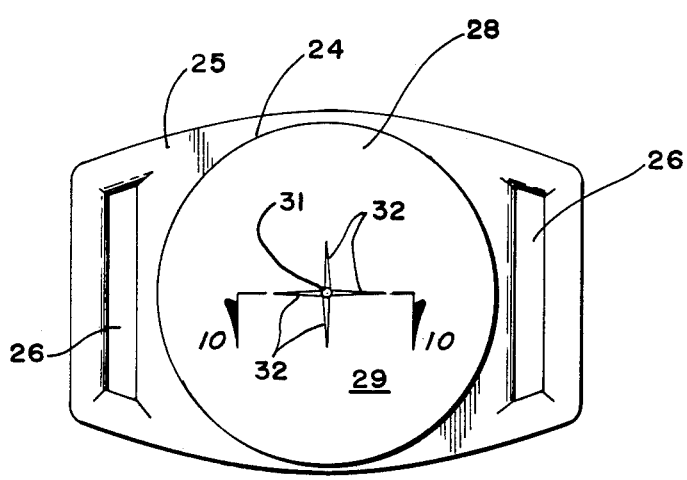

As seen in FIG. 4, sweat is generally collected from the fleshy underside of a patient's forearm 20 or from the fleshy portion of the patient's inner thigh. For convenient application to the limb, strap 16 is preferably provided as two separate lengths provided with means for adjustment, such as by having the material "Velcro" applied to overlapping ends thereof.

When the device is in place on a person's skin, the skin and underlying flesh bulge into the concavity 13 provided by surface 15, FIG. 1.

The outstanding feature of the present invention from an operative standpoint, differentiating it from the earlier Gibson et al. experimental device previously described, is the fact that the concavity backed by the concave, sweat-collecting surface is so shallow as to place the area of skin covered thereby in contact with the sweat-collecting surface over substantially the entire area of the latter, without leaving dead space. We have found that, in this way, sweat, under the pressure at which it is secreted from the sweat glands, is able to rapidly travel across the interface of the skin and collecting surface 15 toward and into bore 18, so that substantially all of the sweat is collected in the flexible tubing 17. Pressure of the collecting surface and rim of the device against the skin should be only that which will effect firm placement against the skin. Excessive tightening of strap 16 is neither necessary nor desirable.

In this embodiment, a diameter of twenty-seven millimeters for the open base of concavity 13, with a depth of one millimeter at the apex, i.e. for the altitude of the preferred squat cone formation, has been found to be very satisfactory, along with collector tubing 17 having an inside diameter of 0.86 millimeters. The cone measurements are regarded as optimum. However, the concavity could have a maximum depth or altitude substantially in the range of from 0.5 to 1.75 millimeters and a diameter substantially in the range of 20 to 35 millimeters. This depth or altitude is in contrast to a depth of 2.5 millimeters in the Gibson et al. experimental device in which significant dead space was present between the sweat-collecting surface and the bulged skin.

In use of the device having the optimum dimensions indicated above, it has been found that about one minute elapses from the time the device is strapped onto an area of the patient's skin that has been stimulated by iontophoretic application of pilocarpine, until sweat appears in collector tubing 17. Once sweat appears, it is possible to see the meniscus of sweat advance in the tubing. If desired, markings may be provided to indicate the volume of sweat collected.

Typically, a volume of about eight microliters of sweat is required for analysis by osmolality or electrical conductivity methods. However, it is desirable to collect an excess of sweat for ease in handling and to allow the analysis to be repeated so as to average out any deviation in salt concentration caused either by variations in the amount of salt contained in various portions of the excreted sweat or by external factors. The present device can easily collect fifty to sixty microliters of sweat from most patients, in a collection time of fifteen minutes.

When a sufficient amount of sweat has been collected, collector tubing 17 is disconnected from axial bore 18, either by pulling it free or by severing it at its emergence from such bore. It should be noted that there is a tendency for a vacuum to form between the collection surface and the skin, so, if the strap is loosened and the device removed with tubing 17 still connected, sweat may be inadvertently withdrawn from the collector tubing and deposited back on the skin. Thus, it is important that the tubing 17 be removed first.

Figure 5:
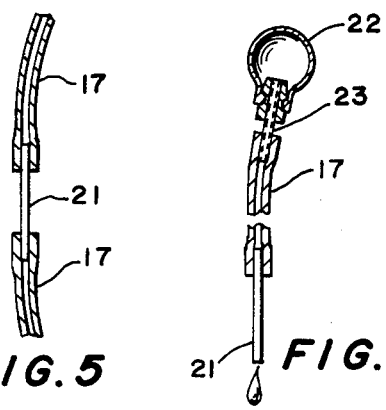

The sweat collected in flexible tubing 17 may be expelled and tested in any convenient way. However, it is advantageous to provide for closing opposite ends of such tubing pending a convenient time for testing to avoid any loss by evaporation or otherwise while carrying the sweat sample to the testing location. For this purpose, a feature of the invention is to employ, as shown in FIG. 5, a relatively short length of rigid tubing 21, such as stainless steel, to connect the opposite open ends of tubing 17.

One end of tubing 17 is removed from rigid tube 21 when the sweat is to be analyzed.

Figure 6:

A further feature of the invention, as shown in FIG. 6, is attachment of one end of tubing 17, after disconnection from rigid tube 21, to an elastomer bulb 22 so that a desired quantity of the collected sweat can be conveniently expelled from collector tubing 17 into a testing vessel. Elastomer bulb 22 is conveniently attached to tubing 17 by means of a second relatively short length of rigid tubing 23, preferably stainless steel corresponding to the rigid tube 21.

FIGS. 7–11 illustrate further embodiments of the invention developed to overcome the problems encountered with infants and adults having very soft skin and flesh.

Although the previously described embodiment of the invention has worked very well in most instances, it has been found that the soft skin and flesh of infants and of some adults protrude into the entrance of bore 18 if the attachment strap is applied too tightly.

The embodiment of FIGS. 7–10 corresponds in most respects with that of the preceding Figs., including a similar sweat-collecting body which has a body portion 24 of disc formation projecting integrally from a back portion formed as a backing plate 25 provided with slot-like openings 26 at opposite ends thereof for the reception of straps constituting means for attaching the device to a person.

Like the previous embodiment, the face of sweat-collecting body portion 24 has a shallow concavity 27 of generally squat, conical shape defined by a concave, sweat-collecting surface 28, but its rim 29 is merely an annular edge in this instance, although it could be a flat annulus as in the previous embodiment. Also, a coiled length of flexible, sweat-collector tubing 30 has one of its ends fitted into a bore 31, which is here shown as counterbored, and extends axially through body portion 24 into communication with concavity 27 at the apex of sweat-collecting surface 28. Here, however, are four symmetrically positioned, relatively short and outwardly tapered, radial ribs 32 formed integrally with body portion 24 and protruding into concavity 27 as barriers to soft skin and flesh blocking the entrance to bore 31.

When the device is in place on a patient, the patient's skin and underlying flesh bulge into concavity 27, but are prevented from blocking sweat flow through bore 31 by the ribs 32 serving as barriers.

Figure 11:
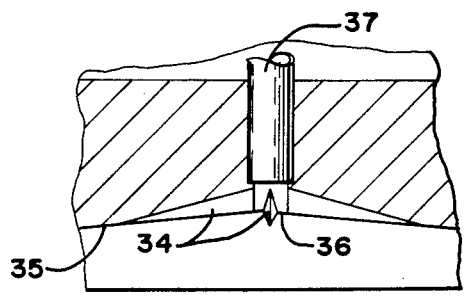

The embodiment of FIG. 11 is similar to that of FIGS. 7–10, except that, instead of ribs protruding into its concavity 33 as barrier means, similarly formed recesses 34 in concave surface 35 are provided for the purpose.

With dimensions of the device being the same as those indicated for the embodiment of FIGS. 1–3, ribs 32 of the embodiment of FIGS. 7–10 are approximately four millimeters in length and protrude approximately 0.33 millimeters from the sweat-collecting surface at the entrance of bore 31, while the recesses are similarly approximately four millimeters in length and approximately 0.33 millimeters in depth at the entrace to bore 36, which is also shown as being counterbored for the reception of tubing 37.

Figure 12:
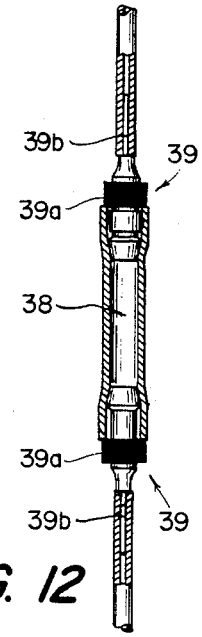
Figure 9:
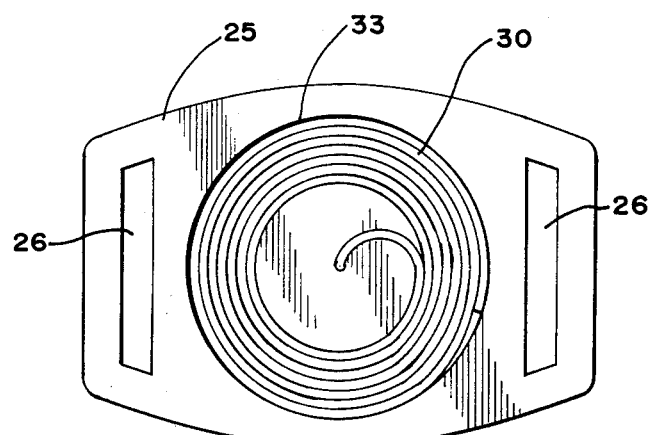
Figure 10:
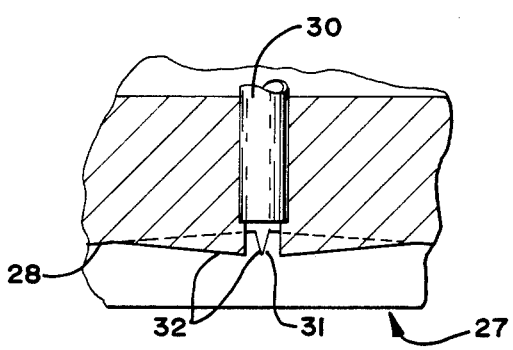

The closed loop tubing arrangement of FIG. 12 is presently preferred over that of FIG. 5, for it provides in itself a pneumatic, elastomer bulb which eliminates the more cumbersome arrangement of FIG. 6. Thus, a relatively short length 38 (about 1½ inches in length) of relatively large diameter (about 5 mm I.D.) flexible plastic tubing, such as a silicone type of plastic, provides the bulb by having its ends attached to respective blunt hypodermic needles 39, such as those marketed by Popper & Sons, Inc., Hyde Park, N.Y., under Part. No. 7402 (Hose Hub 22 gauge by 3/8 blunt), by a close stretch fit over the hubs 39a thereof, leaving the shanks 39b free to receive respective opposite ends of the sweat-filled collector tubing 17 or 30. One of the needles has the opening therethrough closed, as by the application of a drop of epoxy glue to the shank end, and is color-coded at its hub, so the tubing end can be conveniently detached from its shank and used as the discharge spout for the sweat when the bulb 38 is pressed.

Whereas this invention is here illustrated and described with specific reference to embodiments thereof presently contemplated as the best mode of carrying out such invention in actual practice, it is to be understood that various changes may be made in adapting the invention to other embodiments without departing from the broader inventive concepts disclosed herein and comprehended by the claims that follow.

We claim:

1. A sweat-collection device for application to a substantially flat area of the human body, comprising a solid body having concave means defined at a face thereof by a sweat-collecting surface which gradually recedes from a rim lying wholly in a common plane to an axial bore that extends to the opposite face of said solid body, the maximum depth of said concave means being such that the skin and flesh of said flat area of a human body to which the device is applied will bulge into contact with said sweat-collecting surface over substantially the entire area thereof when said rim is placed firmly against the skin of said flat area of the human body, leaving substantially no dead space in the interface between the bulged skin and said sweat-collecting surface, whereby body secretion pressure of sweat will force said sweat through said interface to said axial bore, said bore being adapted to connect with a length of flexible, sweat collector tubing at said opposite face of the solid body, and said solid body being adapted to be fastened against the said flat area of a human body so as to maintain firm placement of said rim and sweat-collecting surface against the skin.

2. A sweat-collection device according to claim 1, wherein the body includes a portion of disc formation which projects from a substantially rectangular portion formed as a backing plate; and wherein there are means at opposite ends of said backing plate for removably receiving an attachment strap.

3. A sweat-collection device in accordance with claim 1, including a length of flexible tubing adapted for connection to the axial bore for collecting sweat therefrom; and a pneumatic bulb arrangement for discharging collected sweat from said tubing, comprising tubular shanks extending from sealed connection with opposite ends of a relatively short, relatively large diameter, flexible tube and adapted to snugly receive opposite ends of said flexible tubing, one of said tubular shanks being closed.

4. A sweat-collection device in accordance with claim 3, wherein the tubular shanks are the needle portions of respective hyperdermic needles having hubs adapted to sealingly receive the opposite ends of the flexible tubing.

5. A sweat-collection device in accordance with claim 3, wherein barrier means are provided at the entrance of the bore for preventing unusually soft skin and flesh from protruding into said bore.

6. A sweat-collection device according to claim 1, wherein the sweat-collecting surface is of squat conical formation.

7. A sweat-collection device according to claim 1, wherein the device includes barrier means at the entrance of the bore for preventing unusually soft skin and flesh from protruding into the bore.

8. A sweat-collection device according to claim 7, wherein the barrier means comprises symmetrically placed, outwardly tapered ribs protruding from the sweat-collecting surface into the concavity and radiating from the opening of the axial bore.

9. A sweat-collection device according to claim 7, wherein the barrier means comprises symmetrically placed, outwardly tapered grooves in the sweat-collecting surface and radiating from the opening of the axial bore.

10. A sweat-collection device in accordance with claim 1, having the opposite face of the body recessed as a chamber for receiving flexible tubing when connected to the axial bore and coiled in flat formation.

11. A sweat-collection device in accordance with claim 10, including a length of flexible tubing normally connected to the axial bore for collecting sweat therefrom and normally coiled in flat, spiral formation within the receiving chamber; and a pneumatic bulb arrangement comprising tubular shanks extending from sealed connection with respective opposite ends of a relatively short, relatively large diameter flexible tube and adapted to snugly receive opposite ends of said flexible tubing, one of said tubular shanks being closed.

12. A method of collecting sweat from a person's skin for testing, comprising the steps of inducing sweating in an area of the person's skin; attaching a sweat-collection device in accordance with claim 1 over said area of the person's skin, with the rim of the sweat-collecting surface placed firmly against said skin; detaching the sweat-collector tubing from the axial bore of the body of the device after sweat has been collected; and closing the ends thereof; and, at an appropriate time thereafter, expelling collected sweat from said tubing into a testing vessel.

13. A method according to claim 12, wherein the ends of the sweat-collector tubing are closed by connecting them to opposite ends, respectively, of relatively short tubular means to form a closed loop.

14. A method according to claim 13, wherein the short tubular means includes a pneumatic bulb intermediate its ends with one of said ends closed and one open; and wherein collected sweat is expelled from the sweat-collector tubing by disconnecting one end thereof from the closed end of the tubular means and pressing said bulb.

15. A sweat collection device, comprising a solid body having concave means at a face thereof defining a sweat-collecting surface which gradually recedes from a rim lying wholly in a common plane to an axial bore that extends to the opposite face of said body so said surface will substantially conform to the bulging of a person's skin and flesh, the maximum depth of said concave means being in the range of from 0.5 to 1.75 millimeters so that the bulged skin will be in contact with said surface over substantially the entire area thereof when said rim is placed firmly against said skin, leaving substantially no dead space in the interface between the bulging skin and said surface, whereby body secretion pressure of sweat will force said sweat through said interface to said axial bore; a length of flexible, sweat-collector tubing whose inside diameter is sufficiently small to substantially preclude evaporation from an open end thereof during sweat collection and having one end connected to said bore at said opposite face of the body so as to receive sweat from said surface; and means for fastening said solid body against the area of skin from which sweat is to be collected, so as to maintain firm placement of said rim and surface against the skin.

16. A sweat collection device according to claim 15, wherein the tubing is coiled in flat spiral formation and the said opposite face of the body is recessed to receive the coiled tubing, said tubing being compactly positioned within the receiving recess but adapted to be extended rectilinearly therefrom.

17. A sweat collection device according to claim 15, wherein the sweat-collecting surface is of substantially conical formation.

18. A sweat collection device according to claim 17, wherein the altitude of the conical formation is within the range of from 0.5 to 1.75 millimmeters and the diameter of the base is within the range of from 20 to 35 millimeters.

19. A sweat collection device according to claim 15, wherein the shallow concavity is of circular formation having a diameter within the range of from 20 to 35 millimeters.

20. A sweat collection device according to claim 15, wherein the concave means is of substantially circular formation, the maximum depth is one millimeter, and the diameter is twenty-seven millimeters; and wherein the inside diameter of the sweat-collector tubing is eighty-six hundreths of a millimeter.

21. A sweat collection device according to claim 15, wherein the solid body includes a portion of disc formation which projects from a substantially rectangular portion formed as a backing plate; and wherein the means for fastening said body to the skin of a person comprises means at opposite ends of said backing plate for removably receiving an attachment strap.

22. A method of collecting sweat from a person's skin for testing, comprising the steps of inducing sweating in an area of the person's skin; attaching a sweat collection device over said area of the person's skin, said device comprising a solid body having concave means defined at a face thereof by a sweat-collecting surface which gradually recedes from a rim lying wholly in a common plane to an axial bore that extends to the opposite face of said solid body, the maximum depth of said concave means being such that the bulged skin will be in contact with said surface over substantially the entire area thereof when said rim is placed firmly against said skin, leaving substantially no dead space in the interface between the bulging skin and said surface, whereby body secretion pressure of sweat will force said sweat through said interface to said axial bore, a length of flexible, sweat-collector tubing whose inside diameter is sufficiently small to substantially preclude evaporation from an open end thereof during sweat collection and having one end connected to said bore at said opposite face of the body so as to receive sweat from said surface, and means for fastening said body against the area of skin from which sweat is to be collected, so as to maintain firm placement of said rim and surface against the skin, the rim of said sweat-collecting surface being placed firmly against said skin; detaching the sweat-collector tubing containing sweat from said body of the device; and expelling the sweat therefrom for test purposes.

23. A method according to claim 22, wherein the ends of the sweat-collector tubing are closed by connecting them to the opposite ends, respectively, of a relatively short length of relatively rigid tubing, to form a closed loop.

24. A method according to claim 22, wherein collected sweat is expelled from the collector tubing by disconnecting one end thereof from the relatively rigid tubing and connecting it to an elastomer bulb by means of a relatively short length of similar rigid tubing.

25. A method according to claim 22, wherein the ends of the detached tubing are closed; and, at an appropriate time thereafter, the sweat is expelled from said tubing into a testing vessel.

26. A method according to claim 22, wherein the collected sweat is expelled from the collector tubing by connecting an end thereof to an elastomeric bulb.

* * * * *